US012805923B2

(12) United States Patent

Karwei et al.

(10) Patent No.: US 12,805,923 B2

(45) Date of Patent: Nov. 24, 2026

(54) ELECTROSURGICAL INSTRUMENT WITH MOVABLE ELECTRODE

(71) Applicant: Erbe Elektromedizin GmbH, Tuebingen (DE)

(72) Inventors: Dietmar Karwei, Ofterdingen (DE); Fabian Bader, Rottenburg (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 855 days.

(21) Appl. No.: 17/872,866

(22) Filed: Jul. 25, 2022

(65) Prior Publication Data

US 2023/0025184 A1 Jan. 26, 2023

(30) Foreign Application Priority Data

Jul. 26, 2021 (EP) .................................... 21187775

(51) Int. Cl.

*A61B 18/14* (2006.01)
*A61B 17/3203* (2006.01)
*A61B 18/00* (2006.01)

(52) U.S. Cl.

CPC ...... *A61B 18/14* (2013.01); *A61B 2018/1405* (2013.01); *A61B 2218/002* (2013.01)

(58) Field of Classification Search

CPC ............ A61B 18/14; A61B 2018/1405; A61B 17/3203

See application file for complete search history.

(56) References Cited

U.S. PATENT DOCUMENTS 4,708,137 A 11/1987 Tsukagoshi
6,193,717 B1 2/2001 Ouchi
2010/0048989 A1* 2/2010 Akahane ............... A61B 1/012 600/104
2013/0296842 A1 11/2013 Anhoeck et al.
(Continued)

FOREIGN PATENT DOCUMENTS

CA 3 137 113 A1 11/2020
CN 101842058 A 9/2010
(Continued)

OTHER PUBLICATIONS

Extended European Search Report dated Jan. 25, 2022, in corresponding European Application No. 21187775.8 with machine English translation.

(Continued)

*Primary Examiner* — Annie L Shoulders

(74) *Attorney, Agent, or Firm* — Fitch, Even, Tabin & Flannery LLP

(57) ABSTRACT

The electrosurgical instrument comprises a basic body configured as a hose or as a hollow rod on which an end piece is configured or into which an end piece is inserted. The end piece comprises a passage channel that comprises a narrowed section at its distal end. The electrode is held in a holder that comprises an extension surrounding the electrode. The extension is configured to extend through the narrowed section of passage channel up to the end surface such that it outcrops at the mouth opening of the narrowed section when the electrode is in the extended position. At this section of extension located at the mouth opening the electrode is connected with the extension.

13 Claims, 3 Drawing Sheets

(56) References Cited

U.S. PATENT DOCUMENTS

| | | | | |
|---|---|---|---|---|
| 2014/0288555 A1* | 9/2014 | Okada | A61B 18/1492 | 606/46 |
| 2016/0008063 A1* | 1/2016 | Wake | A61B 17/3203 | 606/49 |
| 2020/0352643 A1* | 11/2020 | Jensrud | A61B 18/1492 | |
| 2022/0401085 A1* | 12/2022 | Cosman, Jr. | A61B 18/1477 | |

FOREIGN PATENT DOCUMENTS

| | | | |
|---|---|---|---|
| CN | 109310464 | A | 2/2019 |
| CN | 110946643 | A | 4/2020 |
| DE | 3616616 | A1 | 11/1986 |
| EP | 1752108 | A1 | 2/2007 |
| EP | 1726267 | B1 | 8/2008 |
| EP | 2156801 | A1 | 2/2010 |
| EP | 3187137 | B1 | 5/2019 |
| JP | 2014-54372 | A | 3/2014 |
| WO | 2020/070113 | A1 | 4/2020 |
| WO | 2020/154036 | A1 | 7/2020 |
| WO | 2021/015327 | A1 | 1/2021 |

OTHER PUBLICATIONS

Japanese Patent Office; Japanese Notice of Reasons for Refusal in corresponding Japanese Patent Application No. 2022-116307, dated Jun. 30, 2025; 12 pages.

Federal Institute of Industrial Property (FIPS); Russian Office Action in corresponding Russian Patent Application No. 2022119947/14(042004), dated Jul. 16, 2025; 10 pages.

Federal Institute of Industrial Property (FIPS); Search Report in corresponding Russian Patent Application No. 2022119947/14(042004), dated Jul. 16, 2025; 4 pages.

State Intellectual Property Office; Office Action in corresponding Chinese Patent Application No. 202210876105.8, dated Oct. 18, 2025; 20 pages.

* cited by examiner

ELECTROSURGICAL INSTRUMENT WITH MOVABLE ELECTRODE

RELATED APPLICATION(S)

This application claims the benefit of European Patent Application No. 21187775.8, filed Jul. 26, 2021, the contents of which are incorporated herein by reference as if fully rewritten herein.

TECHNICAL FIELD

The invention refers to an electrosurgical instrument, particularly a hybrid instrument that comprises an electrode as well as a fluid nozzle.

BACKGROUND

From DE 36 16 616 A1 an instrument is known denoted as radio frequency cutting device that consists of a hose in the distal end of which a threaded bushing is inserted. The face of this threaded bushing is offset backwardly in proximal direction with reference to the distal face of the flexible hose. The threaded bushing comprises a passage opening that is narrowed at its distal end. An electrode that is held in a holder extends through the narrowed area of the threaded bushing. The holder is located in the passage channel, but does not extend into the narrowed area.

In a further embodiment illustrated in this document the passage channel is conical, wherein the holder is also configured in a conical manner. Also in this embodiment the holder cannot be moved up to the distal end of the instrument or also only into the threaded bushing.

Further, generic prior art is known from EP 1 752 108 A1, EP 2 156 801 A1, EP 1 726 267 B1 and U.S. Pat. No. 6,193,717 B1.

In such instruments the electrode is frequently configured as hollow filigree small tube that is positioned in a retracted position inside the instrument and projects in an extended position from the distal end of the instrument. The electrode is thereby slim, i.e. long in relation to its diameter, and thus subject to the risk of breakage.

It is one object of the invention to provide an improved instrument.

SUMMARY

This object is solved by means of an electrosurgical instrument as described herein.

The instrument according to the invention comprises a distal end piece having a distal end surface and a passage channel, whereby the distal end surface surrounds a mouth opening at which the passage channel opens out. A holder is arranged in the passage channel that is movable linearly in axial direction between a retracted position and an extended position. The axial direction extends from a proximal section of the end piece toward the mouth opening. In the extended position the holder ends flush with the end surface or projects therefrom. A distal end section of the holder comprises a seat opening in which the electrode is arranged. It projects with a section out of the seat opening.

Due to this configuration, the length of the section of the electrode projecting from the holder is minimized, whereby the risk of breakage of the electrode is reduced compared with configurations in which the holder of the electrode remains behind the distal end surface of the end piece, as it is the case in the prior art. In the invention the length of the section of the electrode projecting from the holder is kept as short as possible, whereby the ratio between the length of this section and its diameter (aspect ratio) can be increased. This is particularly of advantage for thin electrodes that are in addition hollow, i.e. that comprise a lumen, with which liquid can be channeled through the electrode and discharged at the distal end thereof. Such electrodes can be manufactured, for example, from tungsten or hard metal by metal injection molding methods (MIM) or by other suitable methods. In the arrangement according to the invention, the holder can serve as heat sink for the electrode that can heat during operation. The heat capacity of the holder serves for cooling the electrode and thus reduces detrimental heat-related phenomena, such as embrittlement of the material of the electrode, adhesion of tissue, forced break durations between subsequent activations and the like. With the inventive configuration the holder can absorb heat emitted from the electrode across short distance.

The concept according to the invention allows the minimization of the length of the electrode. The length of the electrode is composed of the length of the section projecting from the holder and the length of the section held in the holder. If the electrode comprises a fluid channel, its length and therefore its flow resistance is also minimized. Thereby the fluid pressure is reduced that is necessary in order to create a fluid jet at the distal end of the electrode appropriate for sub-tissue injection. Accordingly, the pump power required for supplying the fluid can be reduced.

The concept according to the invention allows a simplified assembly of the electrode. It can be inserted in the holder positioned in the distal end piece and then fixated therein. For fixation of the electrode a laser-welded joint can be used between the electrode and the holder. The laser-welded joint can be applied as soon as the holder is in extended position. The joint site between the holder and the electrode is therefore located in the same plane as the distal end surface of the end piece or even distally in front thereof and is therefore easily accessible.

In a preferred embodiment the passage channel formed in the end piece comprises a narrowed distal section that adjoins a remaining passage channel—that is preferably cylindrical—via a shoulder. The shoulder forms a stop means for the holder, the extension of which extends through the narrowed section. The shoulder can be a ring shoulder. Particularly the shoulder can comprise a planar ring surface or a ring surface that is located on a surface of a cone having an opening angle larger than 90°, preferably larger than 120° or 160°. The ring surface forms a stop surface for the holder. Preferably the extension is at least as long as the narrowed section, such that the end of the extension is flush with the face side distal end surface of the end piece or projects beyond it in the extended position. The seat opening for the electrode extends preferably through the entire extension into the holder.

Further details of advantageous embodiments of the invention are subject of the claims and are further apparent from the drawing and/or the associated description. The drawings show:

DETAILED DESCRIPTION

Figure 1:
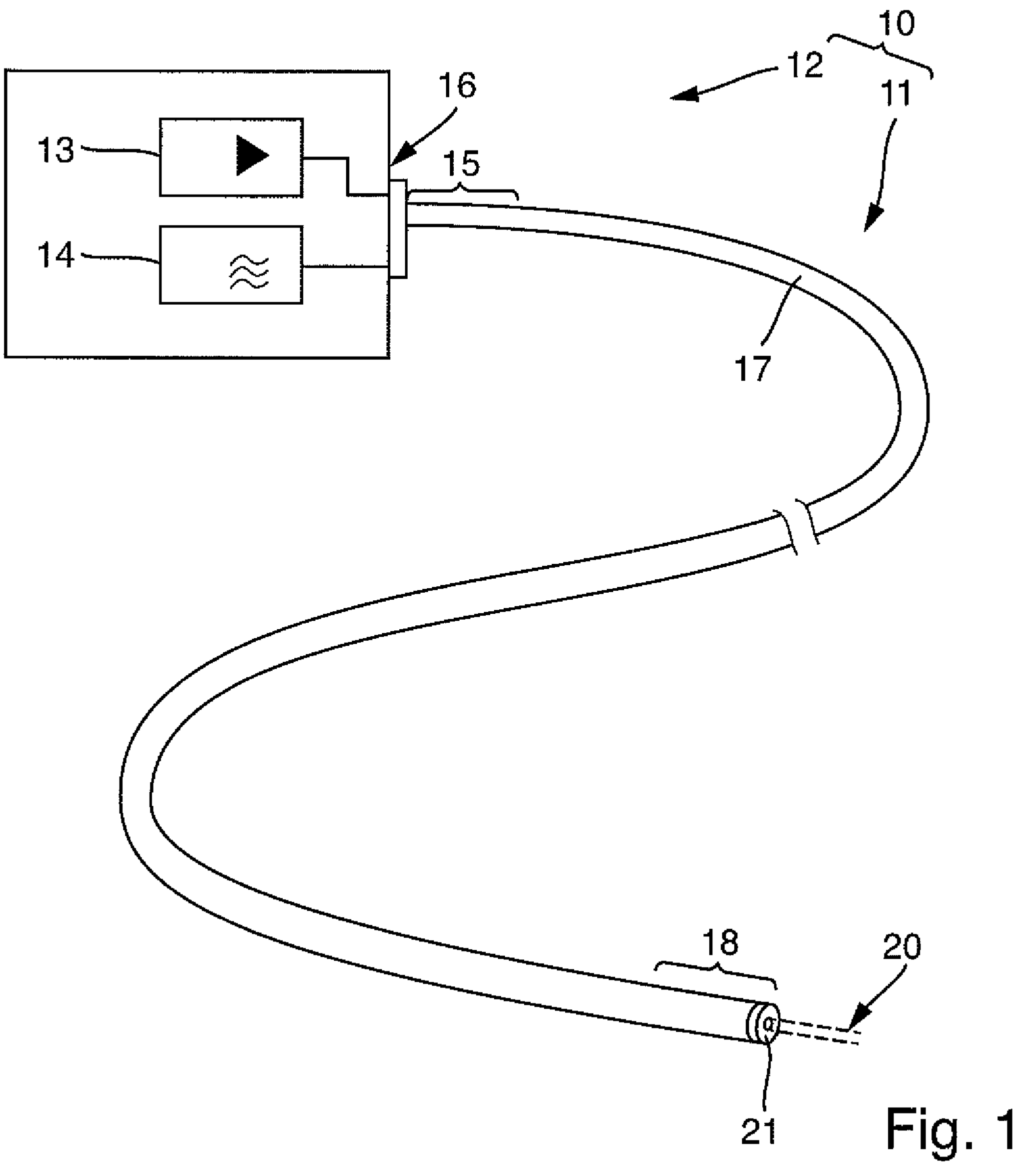
FIG. 1 the instrument according to the invention connected to a supplying apparatus in a schematical illustration, FIG. 2 the distal end of the instrument according to FIG. 12 in an enlarged perspective illustration, FIG. 3 the distal end of the instrument according to FIGS. 1 and 2 in a longitudinally cut basic illustration with the electrode being in operation position (extended position), FIG. 4 the distal end of the instrument according to FIG. 3, however with the holder and electrode being in retracted position, FIG. 5 an illustration in part of the distal end of the instrument in a longitudinally cut enlarged illustration and FIG. 6 a modified embodiment of the instrument according to the invention in an illustration according to FIG. 5.

In FIG. 1 a surgical device 10 is illustrated, whereby an instrument 11 as well as an apparatus 12 provided for supply of the instrument 11 are part of the device 10. The apparatus 12 is configured to provide pressurized fluid, particularly pressurized liquid, such as sodium chloride solution, and comprises a respective supply device 13 for this purpose. In addition, the apparatus 12 comprises a surgical generator 14 that can be configured for emission of radio frequency alternating voltage, for example. The instrument 11 is connected with its proximal end 15 to a respective connection device 16 of apparatus 12 and is therefore supplied with the provided media, e.g. liquid and treatment current. The generator 14 further comprises a non-illustrated neutral connection to which an also not illustrated neutral electrode can be connected that can be attached to a patient.

Figure 2:
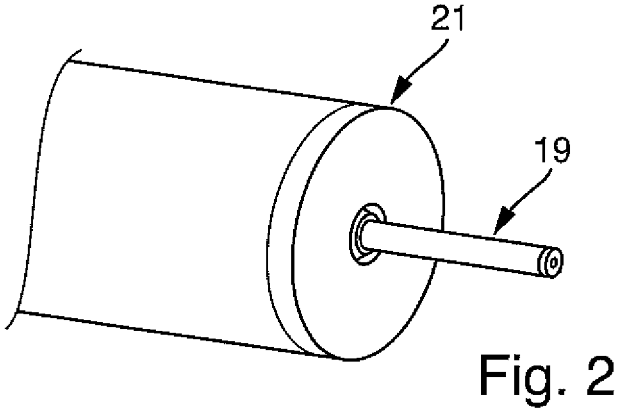

The instrument 11 comprises a flexible hose 17 that extends from the proximal end section of instrument 11 up to its distal end section 18. For example, such an instrument can be used endoscopically in that it is inserted in the body of a patient through the working channel of an endoscope in order to carry out surgical treatments there. The instrument is thereby preferably a hybrid instrument that allows the treatment of tissue by means of a pin or needle-shaped electrode 19 illustrated, e.g. in FIG. 2, as well as the treatment by means of a fluid jet 20 schematically indicated in FIG. 1 by means of which liquid can be introduced into tissue. For example, in this manner liquid reservoirs can be created in biological tissue in order to separate one tissue layer from another tissue layer. One application is the resection of tissue portions in a hollow organ, e.g. the removal of a tumor, during which first a liquid cushion is created below the tumor and the tumor is then cut by means of the electrode 19. Then the liquid cushion separates the tumor from the tissue below in order to allow a careful treatment and removal of the tumor.

Figure 3:
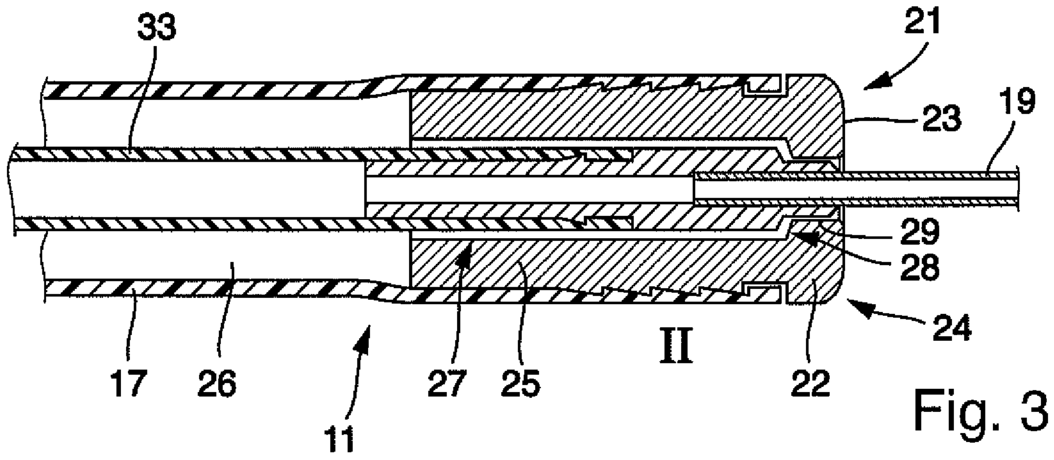
Figure 4:
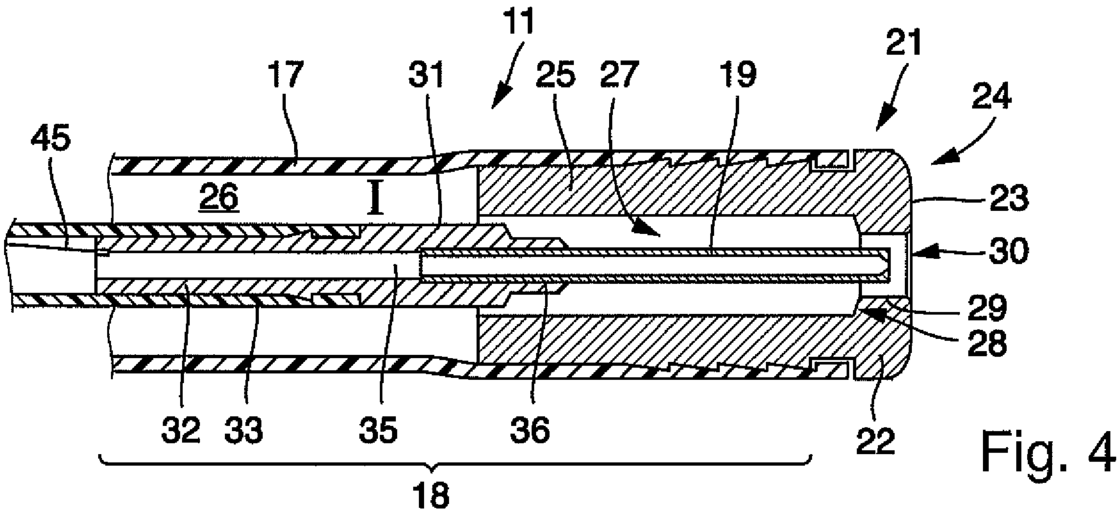

At its distal end section 18 the instrument 11 comprises an end piece 21, the configuration and shaping is particularly apparent from FIGS. 3-6. The distal end piece 21 is configured from ceramic or another preferably non-conductive material, such as a plastic or the like. The end piece 21 comprises a head 22, the face side end surface 23 of which is also the distal end surface of instrument 11. The head 22 is approximately disc-shaped, as apparent from FIG. 2, preferably with a rounded transition 24 from the distal end surface 23 to the circumferential surface. A shank 25 adjoins head 22, wherein the shank 25 is inserted into the lumen 26 of hose 17 which can abut against head 22. The end piece 21 is preferably configured in a rotational symmetric manner with reference to the longitudinal axis of hose 17 and comprises a central passage channel 27. It extends through shank 25 that therefore forms a tube extension. The passage channel 27 is preferably approximately cylindrical. The passage channel 27 narrows at a ring shoulder 28 and then transitions into a diameter reduced section 29 that defines a mouth opening 30 at the end surface 23 (FIG. 4).

Instead of a flexible hose, also a rigid shank can be provided. The end piece 21 can be inserted into the shank or can be part of the shank. It can also be a monolithic component of the hose.

In the distal section 18 of instrument 11 shown in FIGS. 3 and 4 a holder 31 for electrode 19 is arranged. The holder 31 is arranged in the passage channel 27 and longitudinally moveably supported therein. A hose connection extension 32 extends from the holder 31 in proximal direction. On the hose connection extension 32 a fluid hose 33 is held and connected with holder 31 in this manner. The fluid hose 33 extends through the entire length of the instrument up to its proximal end. The fluid hose is preferably configured in a tensile and compression-resistant manner in order to be able to specifically move the holder 31 and the electrode 19 between the retracted position and the extended position from the proximal end of the instrument.

For supply of electrode 19 with treatment current, holder 31 can be provided with current via a wire 45 guided through the lumen of fluid hose 33. The wire 45 is connected with the surgical generator 14 via connection device 16. As an alternative, wire 45 can be arranged inside the wall of fluid hose 33.

The electrode 19 provided with voltage and current respectively can be used for cutting tissue, in that it is pierced in the tissue and is then moved laterally. The voltage applied to the electrode 19 creates sparks between the tissue and the electrode 19 that coagulate and evaporate the tissue. In this manner a cut can be created.

Figure 5:
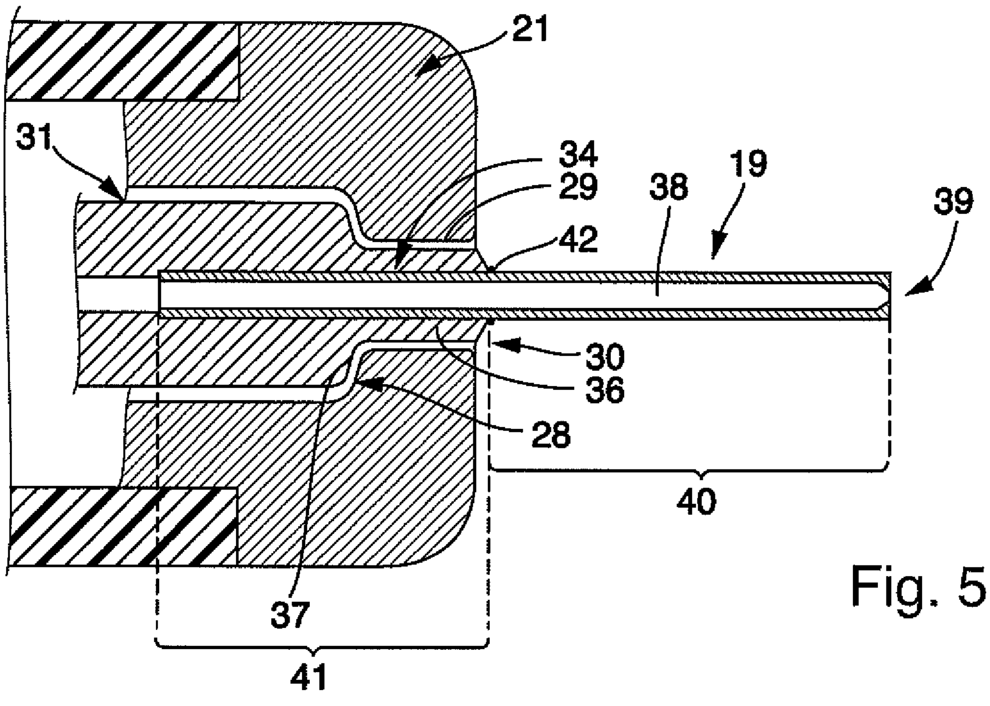

The holder 31 comprises a seat opening 34 that extends coaxially to the holder and the end piece 21 from the distal end into the holder 31, as particularly also apparent from FIG. 5. The seat opening communicates with the fluid channel 35 that extends up to the proximal end of holder 31 through the hose connection extension 32 and thus can be supplied with liquid via fluid hose 33.

The holder 31 comprises a cylindrical section, as apparent from FIG. 5, that is seated with low play axially movable in the passage channel 27. From this cylindrical section an extension 36 extends in distal direction through the diameter reduced section 29 of end piece 21. The extension 36 thereby ends at the mouth opening 30 or slightly projects beyond it, as indicated in FIG. 5.

A shoulder 37 is formed between extension 36 and the remaining section of holder 31, wherein the shoulder can abut against ring shoulder 28. If shoulder 37 abuts against ring shoulder 28, the holder 31 and together therewith electrode 19 are in the extended position according to FIG. 3. If holder 31 is, however, displaced in proximal directions such that electrode 19 is located at or behind the distal end surface 23 in proximal direction, the holder 31 and together with it electrode 19 are in retracted position. The position of holder 31 and electrode 19 can be controlled by means of fluid hose 33 in that it is axially displaced in distal or proximal direction. Respective means for axial movement of fluid hose 33 can be provided on the proximal end 15 or at another location and are not illustrated in the figures.

The electrode 19 can be configured as capillary tube, i.e. as thin wall slim hollow cylinder that surrounds a fluid channel 38. The fluid channel can end in a nozzle opening 39 at the distal end of electrode 19. The nozzle opening 39 can be formed by the open end of the fluid channel 38. As an alternative, the nozzle opening 39 can be formed by a narrowing of fluid channel 38 at its distal end.

The electrode 19 can consist of hard metal, tungsten or the like. It comprises a section 40 projecting from holder 31 and a section 41 held in the seat opening 34. The section 41 is thereby preferably longer than the extension 36 and thus also longer than the diameter reduced section 29. The length of section 40 is preferably multiple times longer than the diameter of electrode 19. Particularly the length 40 is preferably more than 5 times and further preferably more than 10 times as long as the diameter of section 40.

The electrode 19 is preferably connected with holder 31 in a substance bond manner. For this purpose the extension 36 can be connected with electrode 19 by means of one or multiple welded joints 42, particularly at the face side end of extension 36. For example, the welded joint 42 can be a laser-welded joint. The laser-welded joint can comprise a weld seam or one or more weld spots.

Figure 6:
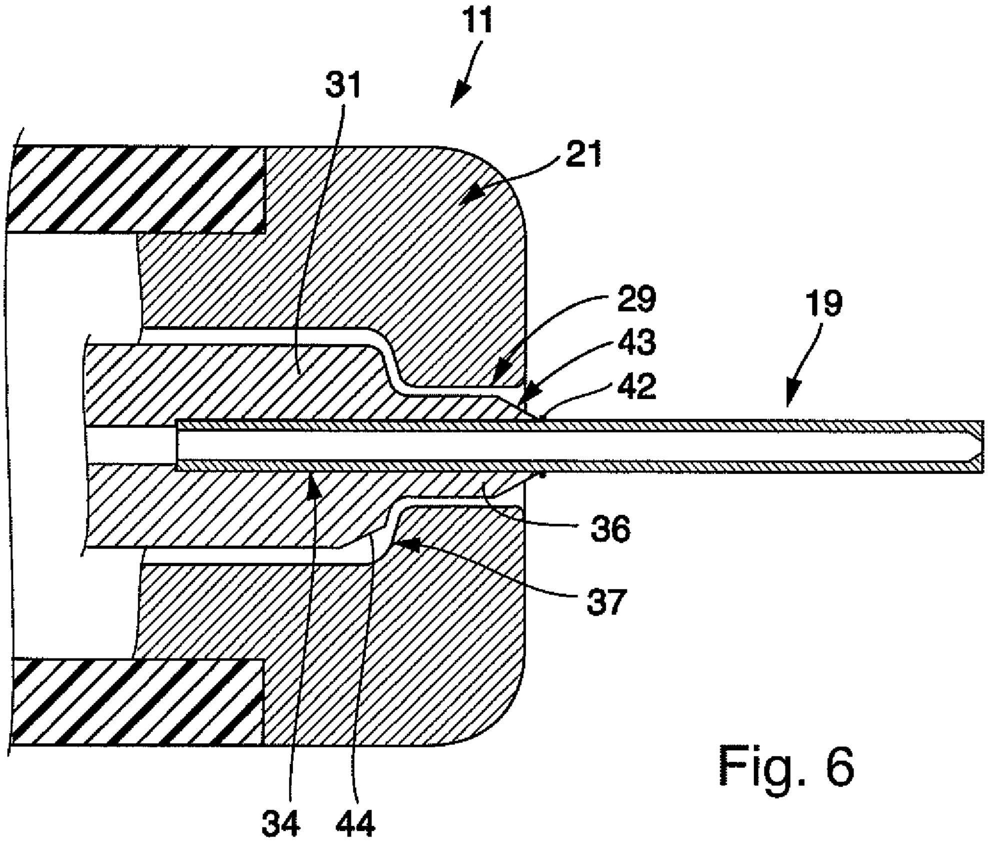

FIG. 6 illustrates instrument 11 described above with the modification described in the following:

At its distal end the extension 36 comprises a conical taper 43 (i.e. a conical section 43) that ends at the weld joint 42. The conical taper 43 can serve as insertion aid, if the holder 41 moves from its retracted position into the extended position and thereby the extension 36 has to enter the diameter reduced section of end piece 21. In addition, the conical section 43 can be used to reduce local stress in the electrode 19 in the vicinity of the weld joint 42, if the electrode 19 is subject to radial forces.

In addition, shoulder 37 can comprise a conical section 44. It serves as insertion aid during insertion of holder 31 into the end piece 21, which simplifies the assembly.

Apart therefrom, the explanations and comments provided to FIGS. 1-5 with reference to the structure and function apply additionally.

The surgical device 10 described so far operates as follows:

During operation instrument 11 is connected to apparatus 12. The respective type of operation, namely sub-injection or resection, is selected by the user by means of non-illustrated control means, e.g. a pedal. The instrument 11 is inserted through an appropriate device, e.g. an endoscope, into the body of the patient. For example, if the surgeon now desires to sub-inject a tissue section, he or she transitions the holder 31 and electrode 19 therewith in the retracted position according to FIG. 4. By activation of the fluid source 13, he or she can supply fluid into the fluid channel 38 of the hollow electrode 19 via fluid hose 33, such that it exits at the nozzle opening 39 in the form of a sharp jet 20. For sub-injection the treating person can place the distal end surface 23 of instrument 11 onto the respective body tissue. The sharp fluid jet 20 penetrates the tissue and creates a liquid reservoir therein.

After this process has been terminated the treating person can switch apparatus 12 and instrument 11 from sub-injection mode into the resection mode. For this holder 31 and therewith electrode 19 are transitioned into the extended position according to FIG. 3, 5 or 6. The holder 31 is thereby moved so far in distal direction that its shoulder 37 gets into abutment against ring shoulder 28. The supply device 13 is deactivated and generator 14 is activated.

With the respective voltage applied and current-applied electrode 19 now a desired tissue section can be cut from the tissue structure, just like with a scalpel and then removed from the body of the patient.

During use of instrument 11 it can be switched between the sub-injection mode and the resection mode in any number of times.

The electrosurgical instrument 11 according to the invention comprises a basic body configured as hose 17 or as hollow rod on which an end piece 21 is configured or into which an end piece 21 is inserted. The end piece 21 comprises a passage channel 27 that comprises a narrowed section 29 at its distal end. The electrode 19 is held in a holder 31 that comprises an extension 36 surrounding the electrode 19. The extension 36 is configured to extend through the narrowed section 29 of passage channel 27 up to the end surface 23 such that it outcrops at the mouth opening 30 of narrowed section 29, if electrode 19 is in the extended position. At this section of extension 36 located at the mouth opening 30 the electrode 19 is connected with, preferably welded to the extension 36.

LIST OF REFERENCE SIGNS

10 surgical device
11 instrument
12 apparatus
13 fluid source
14 surgical generator
15 proximal end section of instrument 11
16 connection device
17 hose
18 distal end section of hose 17
19 electrode
20 fluid jet
21 end piece
22 head
23 distal end surface of instrument 11
24 rounded transition
25 shank
26 lumen of hose 17
27 passage channel of end piece 21
28 ring shoulder
29 diameter reduced section of passage channel 27
30 mouth opening
31 holder
I retracted position of holder 31
II extended position of holder 31
32 hose connection extension
33 fluid hose
34 seat opening
35 fluid channel of holder 31
36 extension
37 shoulder
38 fluid channel of electrode 19
39 nozzle opening
40 distal cantilever section of electrode 19
41 section of electrode 19 held in seat opening 34
42 welded joint
43 conical taper of extension 36
44 conical section of shoulder 37
45 wire

The invention claimed is:

1. An electrosurgical instrument (11), comprising a hybrid instrument with a fluid injection function, the electrosurgical instrument (11) comprising:

a distal end piece (21) that comprises a distal end surface (23) and a passage channel (27), whereby the distal end surface (23) surrounds a mouth opening (30) at which the passage channel (27) opens out, wherein the distal end piece (21) comprises a proximal end and the passage channel (27) extends from the proximal end of the distal end piece to the mouth opening (30) at which the passage channel terminates;

a holder (31) that is linearly movably arranged in the passage channel (27) between a retracted position (I) in which the holder is spaced apart from the distal end surface (23) and an extended position (II) in which the holder (31) ends flush with the distal end surface (23) or projects beyond it, wherein the holder (31) comprises a seat opening (34);

an electrode (19) that is arranged with a first section (41) in the seat opening (34) and a second section (40) that projects distally from the seat opening (34);

wherein the distal end surface (23) of the distal end piece (21) forms a distal end of instrument (11) beyond which the electrode (19) projects in a distal direction when the holder (31) is in the extended position (II); and a welded joint (42) between the holder (31) and the electrode (19) that is flush with or projects distally beyond the distal end surface (23) of the distal end piece (21) when the holder (31) is in the extended position (II).

2. The electrosurgical instrument according to claim 1, wherein the distal end piece (21) comprises a head (22) on which the distal end surface (23) is formed, wherein a shank (25) extends from the head (22) on which a hose (17) is held, wherein the head (22) comprises a head diameter and the shank (25) comprises a shank diameter that is less than the head diameter.

3. The electrosurgical instrument according to claim 2, wherein the holder (31) comprises an extension (36) that extends through the head (22) when the holder (31) is in the extended position (II).

4. The electrosurgical instrument according to claim 3, wherein the passage channel (27) comprises a cylindrical section to which a narrowed section (29) adjoins in a distal direction, wherein the narrowed section (29) ends at the mouth opening (30), and wherein the extension (36) is at least as long as the narrowed section (29).

5. The electrosurgical instrument according to claim 3, wherein the seat opening (34) extends through the extension (36).

6. The electrosurgical instrument according to claim 2, wherein the holder (31) is connected with a fluid hose (33), and wherein the fluid hose (33) is arranged in a manner extending through the hose (17).

7. The electrosurgical instrument according to claim 1, wherein the passage channel (27) comprises a cylindrical section to which a narrowed section (29) adjoins in a distal direction, wherein the narrowed section (29) ends at the mouth opening (30).

8. The electrosurgical instrument according to claim 7, wherein a ring shoulder (28) is formed between the cylindrical section and the narrowed section (29).

9. The electrosurgical instrument according to claim 7, wherein the narrowed section (29) is configured cylindrically.

10. The electrosurgical instrument according to claim 1, wherein the electrode (19) is configured cylindrically.

11. The electrosurgical instrument according to claim 1, wherein the second section (40) of the electrode (19) that projects from the seat opening (34) has a length that is at least five times greater than a diameter of the electrode (19).

12. The electrosurgical instrument according to claim 1, wherein the electrode (19) comprises a fluid channel (38).

13. The electrosurgical instrument according to claim 1, wherein the holder (31) is connected with a fluid hose (33).

* * * * *